United States Patent
Kleppe et al.

(10) Patent No.: US 9,651,766 B2
(45) Date of Patent: May 16, 2017

(54) HIGH-RESOLUTION LUMINESCENCE MICROSCOPY

(75) Inventors: Ingo Kleppe, Jena (DE); Yauheni Novikau, Jena (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 619 days.

(21) Appl. No.: 14/124,462

(22) PCT Filed: May 22, 2012

(86) PCT No.: PCT/EP2012/059466
§ 371 (c)(1),
(2), (4) Date: Mar. 4, 2014

(87) PCT Pub. No.: WO2012/168065
PCT Pub. Date: Dec. 13, 2012

(65) Prior Publication Data
US 2014/0184777 A1 Jul. 3, 2014

(30) Foreign Application Priority Data
Jun. 9, 2011 (DE) .......................... 10 2011 077 269

(51) Int. Cl.
*G02B 21/36* (2006.01)
*G01N 21/64* (2006.01)
(Continued)

(52) U.S. Cl.
CPC ....... *G02B 21/365* (2013.01); *G01N 21/6458* (2013.01); *G02B 21/008* (2013.01);
(Continued)

(58) Field of Classification Search
CPC ............ G01N 21/6458; G02B 21/0076; G02B 21/008; G02B 21/06; G02B 21/365; G02B 27/58
(Continued)

(56) References Cited

U.S. PATENT DOCUMENTS

| | | |
|---|---|---|
| 6,909,105 B1 | 6/2005 | Heintzmann et al. |
| 2010/0303386 A1* | 12/2010 | Enderlein ............ G02B 21/367 382/299 |
| 2011/0284767 A1 | 11/2011 | Wolleschensky et al. |

FOREIGN PATENT DOCUMENTS

| | | | | |
|---|---|---|---|---|
| DE | WO 2010141608 A1 * | 12/2010 | ........... | G02B 21/367 |
| DE | 212009000043 U1 | 1/2011 | | |

(Continued)

OTHER PUBLICATIONS

Claus B. Müller and Jörg Enderlein "Image Scanning Microscopy"Phys. Rev. Lett. 104, 198101, Published May 10, 2010.*

(Continued)

*Primary Examiner* — William C Vaughn, Jr.
*Assistant Examiner* — Naod Belai
(74) *Attorney, Agent, or Firm* — Westerman, Hattori, Daniels & Adrian, LLP (57) ABSTRACT

A microscopy method for generating a high-resolution image (55) of a sample (2) comprising the following steps: a) the sample (2) is provided with a marker, which upon excitation emits statistically flashing luminescent radiation, or a sample (2) is used which upon excitation emits locally distributed, statistically flashing luminescent radiation; b) the sample (2) is excited to luminescence by means of structured illumination, wherein the sample is repeatedly illuminated in at least nine different illumination conditions (0.01-0.09) of the structured illumination by realizing at least three rotary positions, and at least three displacement positions per rotary position of the structured illumination; c) the luminescing sample (2) is repeatedly displayed in each of the different illumination conditions on a flat panel detector having pixels, such that an image sequence (44.01-44.09) is obtained for each of the different illumination conditions (0.01-0.09); d) a raw image, the spatial resolution (Continued)

of which exceeds the optical resolution of the image is generated from each image sequence (44.01-44.09) by means of a cumulant function (46), which evaluates intensity fluctuations of each pixel in the image sequence, said intensity fluctuations being caused by the flashing, so that for each of the different illumination conditions (0.01-0.09), a high-resolution raw image (53.01-53.09) is obtained; e) from the raw images (53.01-53.09) thus obtained, the high-resolution image (55), which relative to the raw images (53.01-53.09) has an increased spatial resolution, is generated by way of computational processing (42) comprising Fourier filtering.

12 Claims, 4 Drawing Sheets (51) Int. Cl.
*G02B 21/00* (2006.01)
*G02B 21/06* (2006.01)
*G02B 27/58* (2006.01)

(52) U.S. Cl.
CPC ......... *G02B 21/0076* (2013.01); *G02B 21/06* (2013.01); *G02B 21/367* (2013.01); *G02B 27/58* (2013.01)

(58) Field of Classification Search
USPC .............................................. 375/240; 348/79
See application file for complete search history.

(56) References Cited

FOREIGN PATENT DOCUMENTS

| WO | 2010/141608 A1 | 12/2010 |
| WO | 2011/135049 A1 | 11/2011 |

OTHER PUBLICATIONS

Notification of Transmittal of Translation of International Preliminary Report on Patentability (Form PCT/IB/338) of International Application No. PCT/EP2012/059466 mailed Dec. 27, 2013 with Forms PCT/IB/373 and PCT/ISA/237.

Stefan W Hell, "Microscopy and its focal switch", Nature Methods, vol. 6, No. 1, Jan. 1, 2009, pp. 24-32.

International Search Report for PCT/EP2012/059466, Mailing Date of Aug. 28, 2012.

* cited by examiner

HIGH-RESOLUTION LUMINESCENCE MICROSCOPY

CROSS REFERENCE TO RELATED APPLICATIONS

This application is a continuation of International Application No. PCT/EP2012/059466, filed May 22, 2012, which claims priority from German Application No. 10 2011 077 269.3, filed Jun. 9, 2011, both of which are incorporated herein by reference in their entireties.

BACKGROUND OF THE INVENTION (1) Field of the Invention

The invention relates to a microscopy method and/or a microscope for generating a high-resolution image of a luminescent sample.

(2) Description of Related Art Including Information Disclosed Under 37 CFR 1.97 and 1.98

The examination of samples using microscopy is a broad technical field for which there are numerous technical solutions. The most varied of the known microscopy methods have developed from the area of classic light microscopy.

A classic area of application of light microscopy for examining biological preparations is luminescence microscopy. In this field, certain dyes (so-called phosphors or florophores) are used to specifically label samples, e.g. cell parts. The sample is illuminated with excitation radiation, as previously mentioned, and the luminescence light created thereby is detected with suitable detectors. Typically, the light microscope is equipped with a dichroic beam splitter together with block filters that divide the fluorescence beam from the excitation beam and enable separate monitoring. This process enables the representation of individual, differently colored parts of the cell in the light microscope. Of course, multiple parts of a preparation may also be marked with different dyes that are absorbed specifically at different structures of the preparation at the same time. This process is known as multiple luminescence. Samples can also be measured that exhibit luminescence on their own, without adding a marker sub stance.

Luminescence in this case, as it is generally known, is a generic term that describes phosphorescence and fluorescence; thus it includes both processes.

In addition, laser scanning microscopy (abbreviated as LSM) is also known to be used to examine samples; it reproduces only that plane that is in the focal plane of the lens from a three-dimensional illuminated image using a confocal detection layout (known as confocal LSM) or nonlinear sample interaction (so-called multiphoton microscopy). An optical cross-section is obtained and the detection of multiple optical cross-sections in various levels of the sample enables the subsequent generation of a three-dimensional image of the sample, composed of various optical cross-sections, with the assistance of a suitable data processing device. Therefore, laser scanning microscopy is suitable for examining thick preparations.

Various approaches have been developed in recent times for resolutions beyond the diffraction limits set by the laws of physics. These microscopy methods are characterized in that they provide users with a higher lateral and/or axial optical resolution as compared to a classic microscope. In this description, such microscopy methods are characterized as high-resolution microscopy methods, because they achieve a resolution beyond the optical diffraction limit. Diffraction-limited microscopes, on the other hand, are characterized as classic microscopes. They utilize known optical wide-field microscopy or laser scanning microscopy.

A high-resolution microscopy method is addressed in U.S. Pat. No. 6,909,105 B1. In this case, nonlinear processes are utilized by means of structured illumination. The saturation of the fluorescence serves to represent nonlinearity. A structured illumination effects a displacement of the object space spectrum relative to the transfer function of the optical system. More specifically, the displacement of the spectrum means that object space frequencies V0 are transmitted at a spatial frequency V0-Vm, where Vm represents the frequency of the structured illumination. At a given spatial frequency that is maximally transferable by the system, this enables the transfer of spatial frequencies of the object that are greater by the amount of the displacement frequency Vm than the maximum frequency of the transfer function. This approach requires Fourier filtering as a reconstruction algorithm for creating images and the evaluation of multiple views for an image. U.S. Pat. No. 6,909,105 B1, which is likewise fully incorporated by reference herein with respect to the corresponding description of the resolution microscopy method, thus uses structured wide-field illumination of the sample, for example via an amplitude/phase grating.

Fluorescence in the sample is also detected using wide-field microscopy. The grating is then placed into three different rotational positions, e.g. 0°, 120°, and 240°, and the grating is then displaced into three or more different positions within each rotational position. Wide-field microscopy is used on the sample in each of the displacements of the three rotational positions (i.e. for a total of at least 9 illumination states). Furthermore, the grating has frequencies as close as possible to the limit frequency that the optical layout used is capable of transferring. The above-mentioned displacement then takes place with the use of Fourier filtering, whereby particularly the 0 and +/−1 diffraction layouts in the images are evaluated. This microscopy method is also known as the SIM method.

An increase in the resolution is obtained with this principle when the structuring (e.g. by means of a grating) is intensive to the extent that the fluorescence in the sample achieves saturation in the bright areas. The structured illumination of the sample no longer has a sinusoidal distribution on the sample but rather an even higher harmonic one beyond the optical limit frequency due to the saturation effects. This additional development of the SIM method is also known as saturated pattern excitation microscopy (SPEM).

Further development of the SIM method can also be achieved with a line-type illumination that is perpendicular to the direction of the grating. A linear illumination is then achieved in which the grating structure is reproduced along the line. The line of the illumination is thus, on its part, structured by the grating. The line-type illumination enables confocal slit detection and thus another increase in resolution. This method is also abbreviated as SLIM.

The publication by C. Müller and J. Enderlein, "Image scanning microscopy," Physical Review Letters, 104, 198101 (2010), addresses the SIM principle, but utilizes scanning of the sample with confocal illumination and detection with subsequent Fourier filtration. This principle is known as ISM. With this method, there are not nine orientations of a structured illumination but instead each scan position, i.e. each grating state when an image is scanned, corresponds to an illumination state and the structured illumination is a spot illumination of the sample.

The publication from T. Dertinger, et al., "Fast, background-free, 3-D super-resolution optical fluctuation imaging (SOFI)," PNAS (2009), page 22287-22292 and "Achieving increased resolution and more pixels with Super-resolution Optical Fluctuation Imaging (SOFI)," Opt. Express, 30 Aug. 2010, 18(18): 18875-85, doi: 10.1364/IE.18.018875 and S. Geissbuehler et al., "Comparison between SOFI and STORM," Biomed. Opt. Express 2, 408-420 (2011), discloses a further high-resolution method of luminescence microscopy. This method utilizes the flashing properties of a fluorophore. If the fluorophores of a sample are flashing statistically independently of one another, a reproduction of the sample can be achieved through filtration with a so-called cumulant function as well as a significant increase in the resolution beyond the given physical resolution limit. An example of such a cumulant function is the second-order autocorrelation function. To generate a high-resolution image in this case, a series of individual images is acquired and combined to create a single image, which then has the higher resolution, using the cumulant function. This method is abbreviated as the SOFI method that stands for "Super-Resolution Optical Fluctuation Imaging."

Combining multiple high-resolution microscopy methods is further known in prior art. Thus, for example, US 2011/0284767 A1 describes combining various high-resolution microscopy methods with the goal of being able to use the particular method that is optimum for each individual sample area in terms of resolution and measuring speed.

BRIEF SUMMARY OF THE INVENTION

The object of the invention is to provide a microscopy method or a microscope that increases resolution.

This object is achieved according to the invention with a microscopy method for creating a high-resolution image of a sample, in which the method has the following steps: a) the sample is given a marker that emits statistically flashing luminescent radiation after excitation, or a sample is used that emits locally distributed, statistically flashing luminescent radiation; b) the sample is excited to the state of luminescence through structured illumination, during which the sample is repeatedly illuminated in various states of illumination of the structured illumination; c) the luminescent sample is reproduced repeatedly onto a detector in each of the various illumination states so that an image sequence is obtained for each of the various illumination states; d) a raw image, which has local resolution beyond the optical resolution of the image generated, is created from each sequence of images using a cumulant function, which evaluates intensity fluctuations in the sequence of images caused by the flashing, so that a high-resolution image is obtained for each of the various illumination states; e) the high-resolution image, which has a local resolution higher than that of the individual images, is generated from the raw images obtained through computer processing comprising Fourier filtration.

The object is further achieved according to the invention with a microscopy method for creating a high-resolution image of a sample, in which the method has the following steps: a) the sample is given a marker that emits statistically flashing luminescent radiation after excitation, or a sample is used that emits locally distributed, statistically flashing luminescent radiation; b) the sample is excited to the state of luminescence through structured illumination, during which the sample is repeatedly illuminated with a set of various states of illumination of the structured illumination; c) the luminescent sample in each set and there in each of the various illumination states is reproduced repeatedly onto a detector so that a sequence of sets, each of which comprise one image for each different illumination state, is obtained; d) a raw image, which has local resolution beyond the optical resolution of the image generated, is created from each set through computer processing comprising Fourier filtration, so that a sequence of raw images is obtained; e) the high-resolution image, which has a local resolution higher than that of the raw images, is generated from the sequence of raw images using a cumulant function, which evaluates intensity fluctuations in the sequence caused by the flashing.

The object is additionally achieved with a microscope for creating a high-resolution image of a sample, in which the sample is provided with a marker that emits statistically flashing luminescent radiation after excitation, or a sample is used that emits locally distributed, statistically flashing luminescent radiation after excitation in which the microscope comprises the following: a detection beam path and an illumination beam path, in which the detection beam path reproduces the sample on the detector and the illumination beam path illuminates the sample to a state of excitation of luminescence through structured illumination, during which the illumination beam path has a device for implementing various illumination states; a computing and control device that controls the microscope such that the sample is repeatedly illuminated with the various illumination states of the structured illumination, and the illumination sample is repeatedly reproduced onto a detector in each of the various illumination states so that a sequence of images is obtained for each of the various illumination states; the computing and control device generates a raw image, which has local resolution higher than the optical resolution of the image obtained, from each sequence of images by means of the cumulant function, which evaluates the intensity fluctuations in the sequence of images caused by the flashing; the computing and control device generates the high-resolution image, which has increased local resolution as compared to the individual images, from the raw images obtained through computer processing comprising Fourier filtration.

The object is finally also achieved with a microscope for creating a high-resolution image of a sample in which the sample is provided with a marker that emits statistically flashing luminescent radiation after excitation, or a sample that emits locally distributed, statistically flashing luminescent radiation after excitation, in which the microscope comprises the following: a detection beam path and an illumination beam path, in which the detection beam path reproduces the sample [onto] the detector and the illumination beam path illuminates the sample to a state of excitation of luminescence through structured illumination, during which the illumination beam path has a device for implementing various illumination states; a computing and control device that controls the microscope such that the sample is repeatedly illuminated with a set of various illumination states of the structured illumination, and the luminescent sample is repeatedly reproduced in each set and there in each of the various illumination states onto the detector so that a sequence of sets, each of which comprises one image for each different illumination state, is obtained; the computing and control device generates a raw image from each set that has local resolution higher than the optical resolution of the image obtained, due to computer processing comprising Fourier filtration, so that a sequence of raw images is obtained; the computing and control device generates the high-resolution image, which has increased local resolution as compared to the raw images, from the sequence of raw images by means of a cumulant function, which evaluates the intensity fluctuations in the sequence caused by the flashing.

According to the invention, elements of the SIM/ISM principle are combined with elements of the SOFI principle. A clever combination will achieve an increase in resolution that is better than the factor of $\sqrt{2}$, which would result from a combination of the individual high-resolution images. The image has a higher resolution than the average of images of the individual method features by themselves achieves, with the same effort.

When the SIM principle is utilized, the sample is illuminated in at least nine different illumination states of the structured illumination in that at least three rotational positions and at least three displacement positions of the structured illumination per rotational position are realized. The luminescent sample is repeatedly reproduced onto a surface detector having a pixel in each of the different illumination states. The intensity fluctuations in the sequence caused by the flashing are evaluated for each pixel.

When the ISM principle is utilized, the illumination states are the different scan positions that occur during scanning. In contrast to conventional LSM, the images of the sample in the different illumination states have a resolution that shows the structure of the fluorescent elements. This can, for example, be carried out through wide-field detection with suitable resolution.

The images of the florescent sample obtained with the various illumination states then represent a set of images. The acquiring of said sets is repeated in order to obtain a sequence of sets. A high-resolution image can then be obtained from this sequence of sets in two ways:

1. Each set can be converted into a high-resolution raw image by means of the computer processing known for SIM/ISM while using Fourier filtration. This will result in a sequence of raw images. This sequence of raw images is then converted into a final image with even higher resolution using a cumulant function according to the SOFI approach. The resolution of the final image in this case is significantly increased compared to that of the raw image. In particular, the result is a resolution that is significantly better than would be obtained through a simple combination of images that would be obtained with the SIM or SOFI principles.
2. The sequence of sets, each of which comprises one image of the sample in the various illumination states, can, however, first be converted into a set of raw images, which contains one raw image for each illumination state, by means of the SOFI principle with the use of the cumulant function. This set comprising raw images can then be converted into a final image that also has increased resolution by means of the SIM/ISM approach.

Because the invention comprises features of the SIM principle, the following documents, which include details of the SIM principle, are incorporated herein in their entirety: U.S. Pat. No. 6,909,105 A1, M. Gustafsson, "Nonlinear Structured-illumination Microscopy: Wide-field fluorescence imaging with theoretically unlimited resolution," Proc Natl Acad Sci USA, 13 Sep. 2005, 102(37): 13081-6, Epub 2 September 2005; R. Heintzmann and C. Cremer, (1998), Proc. SPIE Int. Soc. Opt. Eng. 3568, page 185-195. The same thing applies to the ISM publication from C. Müller and J. Enderlein, "Image Scanning Microscopy," Physical Review Letters, 104, 198101 (2010).

Because the invention also uses features of the SOFI principle, the following publications relevant for this principle are also fully incorporated herein: T. Dertinger, et al., "Fast, background-free, 3-D super-resolution optical fluctuation imaging (SOFI)," PNAS (2009), page 22287-22292 including all of the corresponding "Supporting Information"; "Achieving increased resolution and more pixels with Super-resolution Optical Fluctuation Imaging (SOFI)," Opt. Express, 30 Aug. 2010, 18(18): 18875-85, doi: 10.1364/IE.18.018875 and S. Geissbuehler et al., "Comparison between SOFI and STORM," Biomed. Opt. Express 2, page 408-420 (2011).

According to the invention, the sample is given a marker that emits statistically flashing luminescent radiation after suitable excitation. Markers in this case are understood to be customary labels or other substances that are taken up by structures of the sample to be represented. Alternatively, a sample that is already suitably luminescent can be used. Finally, a sample is microscopically reproduced having structures that emit statistically flashing luminescent radiation. "Statistically flashing" in this case means that the individual markers or sample molecules each switch between two luminescent radiation states, independently of adjacent markers or molecules. In the simplest case, this may be a state in which luminescent radiation is emitted and a state in which no luminescent radiation is emitted. However, the switch between the emitting of two different types of luminescent radiation is also possible, for example a wavelength change, a polarization change, etc. This property of the sample is necessary for using the elements from the SOFI principle, because only then will the cumulant function enable a series of images to be converted into a single high-resolution image.

If the second variant as mentioned above is used in which a sequence of sets of images of the sample in various illumination states is converted into a sequence comprising high-resolution raw images by means of the Fourier transformation, the flashing properties within a set should not change to the extent possible. The result is that the duration in which a set is acquired, measured at the average flashing frequency, should be short, i.e. no longer than the inverse of the flashing frequency or especially preferably a fraction of the inverse. This corresponds to the feature that the set rate be less than, preferably 10 times less than, the average image frequency. This will ensure that the flashing state of the participating molecules will not change within a set. This is advantageous for the SOFI processing carried out on the sequence of raw images.

Therefore, it is advantageous in a further embodiment of the invention if the image acquisition speed and the flashing rate of the molecules used are suitably adapted to one another. One way to achieve this is by selecting suitable marker or sample molecules. Of course, it is also possible to adapt the flashing rate of the molecules through suitable manipulation. Depending on the molecule, various physical influencing variables come into play here, particularly temperature, wavelength of the illumination radiation acting as the excitation radiation, intensity of the illumination radiation acting as the excitation radiation, etc. Chemical influences are also possible such as, for example, those explained by Geissbuehler et al. Furthermore, the image acquisition period or set rate (rate of sets with images) can be adapted accordingly for a given flashing rate in order to achieve the aforementioned state.

To the extent that the invention is described in the previous or subsequent text with reference to features of the method, this should apply uniformly to the description of a corresponding microscope comprising the aforementioned features. For the microscope, it is essential that its computing and control device ensure corresponding operation of the microscope for implementing the method features mentioned. The computing and control device is suitably designed for this, for example through suitable programming. The reverse applies as well of course in the event that individual features should only be described by means of the microscope. The features then apply analogously for the microscopy method described.

For SIM, SLIM, and SPEM, a rotation of the structured illumination is required, as has been previously explained. This can be implemented in a particularly simple manner if the grating for implementing this microscopy method lies in the same cross-section as the second and third beam path of illumination and an image field rotator is downstream. This can be implemented with an Abbe-Koenig prism, for example. Said downstream image field rotator is particularly advantageous for the SLIM principle because then the perpendicular position of the grating and the line-type illumination only has to be adjusted once and any tracking that would otherwise be required with grating rotation can be dispensed with.

It is clear that the previously- and subsequently-mentioned features to be explained can be used not only in the combinations indicated but also in other combinations or alone without going beyond the scope of the present invention.

BRIEF DESCRIPTION OF THE SEVERAL VIEWS OF THE DRAWINGS

The invention will be explained in greater detail in the following by means of the enclosed drawings, which also disclose inventive features. The following is shown.

DETAILED DESCRIPTION OF THE INVENTION

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

Figure 1:
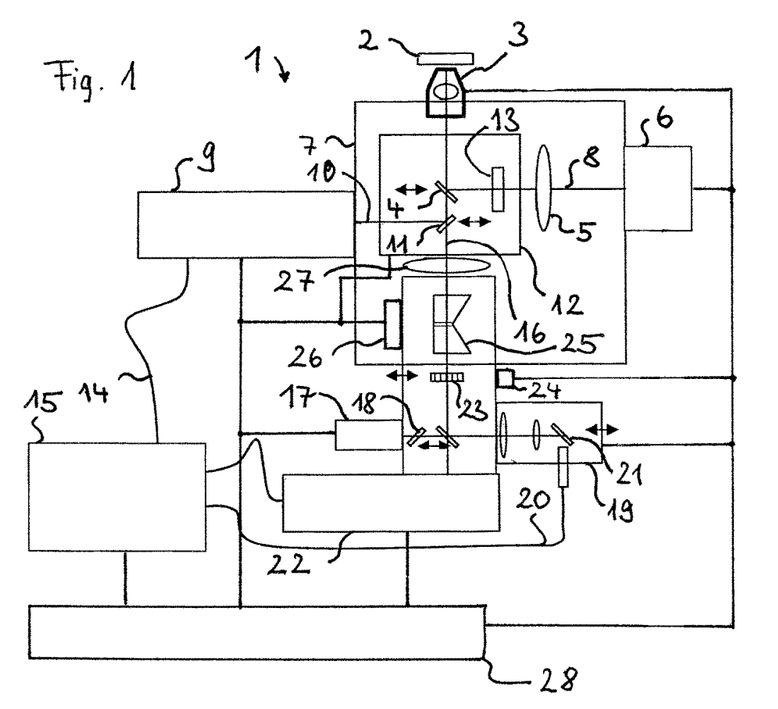
FIG. 1 shows a schematic representation of a compound microscope.

FIG. 1 shows a microscope 1, the classic microscopy method, i.e. the microscopy method whose resolution is diffraction-limited, where the high-resolution microscopy method can be executed simultaneously, i.e. with a microscopy method whose resolution has increased beyond the diffraction limit.

The microscope 1 is based on a conventional laser scanning microscope (LSM) and acquires a sample 2. To this end, it has a lens 3 through which the beam extends for all microscopy methods.

Using a beam splitter 4, the lens 3 reproduces the sample, together with a tube lens 5, onto a CCD detector 6, which is a generally available surface detector in the example. In this respect, the microscope 1 has a conventional light microscope module 7, and the beam path from the sample 2 through the lens 3 and the tube lens 5 to the CCD detector 6 corresponds to a conventional wide-field detection beam path 8. The beam splitter 4 is switchable, as indicated by the double arrow in FIG. 1, in order to enable switching of the beam splitters with various dichroic properties or achromatic beam splitters according to US 2008/0088920.

The beam path to the lens 3 also has a laser scanning module 9 included whose LSM illumination and detection beam path is fed into the beam path to the lens 3 via a switching mirror 11, which also has beam splitter functions. The beam path from the switching mirror 11 to the lens 3 through the beam splitter 4 is thus one beam path in which the illumination beam path and the detection beam path are combined. This also applies with respect to the laser scanning module 9 as well as the wide-field detection beam path 8 because, as will be explained, illumination radiation is also fed into the switching mirror 11, and the illumination radiation together with the wide-field detection beam path 8, i.e. with the CCD detector 6, accomplishes the microscopy method.

The switching mirror 11 and the beam splitter 4 are combined into a beam splitter module 12, whereby it is possible to switch the switching mirror 11 and the beam splitter 4 depending on the application. The double arrow also indicates the switching capabilities of the mirror 11 and splitter 4. The beam splitter module 12 also has an emission filter 13, which is in the wide-field detection beam path 8 and which suitably filters spectral portions that could propagate through the wide-field detection beam path 8. Of course, the emission filter 13 in the beam splitter module 12 is also switchable.

The laser scanning module 9 receives the laser radiation required for operation from a laser module 15 via a light-conducting fiber 14.

In the design shown in FIG. 1, a collector illumination beam path 16 is fed onto the beam splitter module 12, or more precisely onto the switching mirror 11, through which illumination radiation extends for various microscopy methods. Various illumination beam paths of individual illumination modules are fed into this collector illumination radiation beam 16. For example, a wide-field illumination module 17 feeds wide-field illumination radiation into the collector illumination radiation path 16 via a switching mirror 18, so that the sample 2 undergoes wide-field illumination via a tube lens 27 and the lens 3. The wide-field illumination module can have, for example, an HBO bulb.

An additional illumination module is a TIRF illumination module 19, which provides TIRF illumination when the switching mirror 18 is adjusted correctly. To this end, the TIRF illumination module 19 receives radiation from the radiation module 15 via a light-conducting fiber 20. The TIRF illumination module 19 has a mirror 21 that can be moved longitudinally. Due to the longitudinal movement, the illumination beam that is emitted from the TIRF illumination module 19 is displaced perpendicularly with respect to the main diffusion direction of the emitted illumination beam, thereby enabling the TIRF illumination to be within an adjustable angle with respect to the optical axis of the lens, that the results on the lens 3. In this manner, the necessary angle of the total reflection can be easily assured on the cover glass. Of course, other ways are also suitable for accomplishing this angle adjustment.

Furthermore, the illumination beam path of a manipulator module 22 is fed to the collector illumination beam path. The manipulator module 22 also receives radiation via a light-conductor fiber (not described in more detail) from the laser module 15 and carries out a dotted or line-type beam distribution in the form of scanning over the sample 2. The manipulator module essentially corresponds to the illumination module of a laser scanning microscope and accordingly the manipulator module 22 can also be operated in combination with the detector of the laser scanning module 9 or the wide-field detection of the CCD detector 6.

The collector illumination beam path 16 also has a grating 23 whose grating constant is below the limit frequency that can be transferred to the sample 2 with the microscope 1. The grating 23 can be moved laterally with respect to the optical axis of the collector illumination beam path 16. To this end, a corresponding feed drive 24 is provided.

In the illumination direction downstream of the grating, there is additionally an image field rotator 25 in the collector illumination beam path 16, which is rotated by a rotator drive 26. The image field rotator can be, for example, an Abbe-Koenig prism.

The modules and drives as well as detectors in the microscope 1 are all connected to a control device 28 via cables, which are not further described. This connection can be implemented, for example, via a data bus and control bus. The control device 28 controls the microscope 1 in various operating modes.

The control device 28 thus enables the realization of classic microscopy on the microscope 1, i.e. wide-field microscopy (WF), laser scanning microscopy (LSM), and also fluorescence microscopy with total internal reflection (TIRF). The microscope in FIG. 1 essentially has two modules suitable for laser scanning illumination, namely the laser scanning module 9 and the manipulator module 22. Of course, other combinations are also possible. These modules are fed with illumination via tube lenses to the lens 3, onto the sample 2. The manipulator module 22 only contains the excitation part of a laser scanning module, without detection. Thereby the sample can be illuminated in the form of dots and the illumination spot can be scanned above the sample 2. It is preferable if a switching unit is also located in the manipulator module 2, e.g. a switching lens or cylinder lens that can be used to switch between a dotted and a line-type illumination. This line-type illumination is then especially advantageous when the grating 23, which is located in an intermediate image of the collector illumination beam path 16, is swiveled in and lies perpendicular to the line of the line-type illumination.

As an alternative to the grating 23, a variably adjustable strip modulator or a DMD can be used to create a structured illumination in the sample 2. Then the feed drive 24 and the swivel in/out function of the grating 23 are of course no longer necessary.

The image field rotator 25 enables the structured illumination created by the grating 23 (or the elements replacing it) to be rotated around the optical axis of the collector illumination beam path 16 so that the structured illumination lies within various angles in the sample 2.

In order to switch between individual operating modes, the switching mirrors 18 and 11, and the beam splitter 4 are suitably adjusted. To this end, folding or swiveling mirrors can be used in the implementation so that a switchover can take place sequentially between the operating modes. Alternatively, dichroic mirrors that enable simultaneous operation of the various modules are also possible.

The beam splitter 4 is preferably designed as a dichroic beam splitter, in which the spectral properties are adjustable such that the spectral portions of fluorescence emissions by the marking molecules, which are to be detected with the assistance of the CCD detector 6, reach the wide-field detection beam path 8, and the remaining spectral components are transmitted to the extent possible. To increase the flexibility with respect to usability of the marking molecules with various emissions characteristics, multiple various beam splitters 4 and emission filters 13 are arranged to be exchangeable on the beam splitter module 12, e.g. on a filter wheel.

The aforementioned microscope is then ready to create a high-resolution microscopic image. To this end, the control device 28 is designed in a suitable manner, for example, through suitable programming. Before potential method sequences are explained by means of FIGS. 4 and 5, essential features and principles that are components of the microscopy methods to be described are explained by means of FIGS. 2 and 3.

Figure 2:
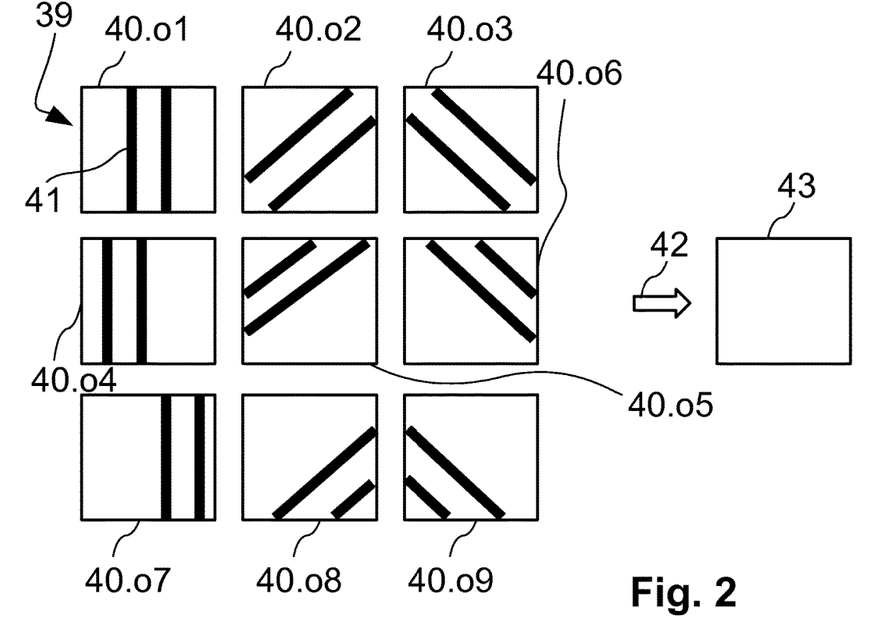
FIG. 2 shows a schematic representation to clarify the creation of a high resolution image comprising multiple wide-field images of a sample that were obtained under various illumination states.

FIG. 2 shows an example of the SIM concept. To this end, the sample undergoing microscopy in the microscope 1 in FIG. 1 is reproduced repeatedly through the wide-field method, during which different illumination states are set for each image. This results in a set 39 of individual images 40. The images 40 differ with respect to structuring 41 of the illumination that is applied to the sample by the illumination beam path 8. As can be seen, the structuring 41 is different in various images 40. As the set 39 shown in the top view in FIG. 2 shows, there are total of nine individual images; thus there are nine different orientations of the structuring 41. The different types of structuring are shown in the representation in FIG. 2 by appending ".O1" to ".O9" to reference number 40 of the respective image. The top view of the individual images 40 in FIG. 2 shows that the nine orientations differ with respect to a displacement position or a rotational position of the structuring 40. The number nine is an example of the orientations used. It is also possible to have a higher number, as this is known from the publications on the SIM principle listed herein.

The individual images 40 of the set 39 are acquired sequentially during which the illumination is displaced or rotated accordingly between the capture of each image 40.

A high-resolution image 43 is then created from the entire set 39 by means of a Fourier transformation 42. This image 43 can be used as a raw image for further high-resolution processing, as is explained in the following by means of FIG. 4.

FIG. 2 thus shows features of the SIM principle. The structuring 41 should be understood, however, to be purely as an example. In particular, it does not have to be a line-type structuring. In addition, the lines shown schematically can be even further structured along the line.

In a similar manner, it is also possible to use scanned confocal dotted illumination with confocal detection, instead of the line-type illumination used in the SIM publications mentioned at the beginning, as is known from the publication from C. Müller and J. Enderlein, "Image scanning microscopy," Physical Review Letters, 104, 198101 (2010). This principle is known as ISM. Of course, there will then not be nine orientations in a structured illumination but rather a suitable plurality of individual images that were obtained from the scanning of a sample. Each image 40 then corresponds to a certain scanned position, i.e. a certain grating state during the scanning of the image.

Figure 3:
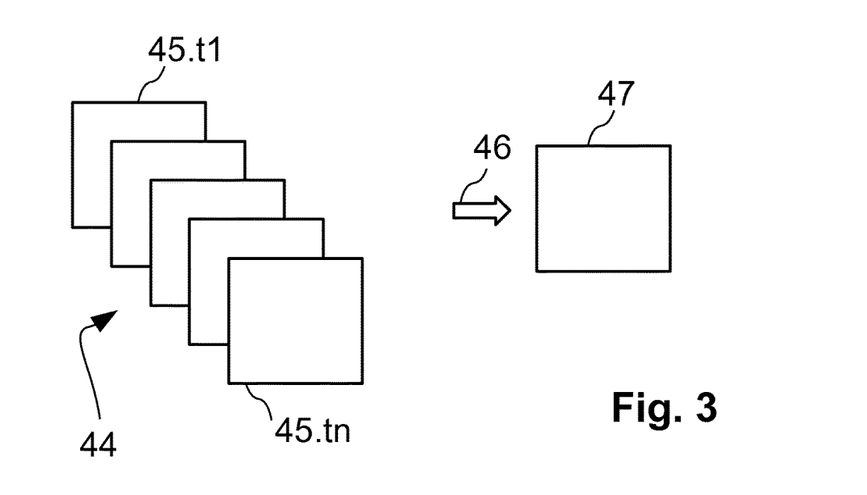
FIG. 3 shows a schematic representation to illustrate the creation of a high resolution image comprising a sequence of images of the sample in various flashing states while combining the principles according to FIGS. 2 and 3.

FIG. 3 is a schematic representation of an additional principle that is used for high-resolution microscopy. According to this principle, a sequence 44 of images 45 is acquired during which, as explained at the beginning with reference to the SOFI concept, each image 45 contains a different flashing state of the fluorophores in the sample 2. The fact that the sequence 44 is a time sequence is indicated by the suffixes that are appended to the reference number 45 for the images. The individual images have the suffix ".t1" to ".tn". A high-resolution raw image 47 is then created from the sequence 44 using a process that utilizes a cumulant function 46. The n images 45 are thus converted into a single image 47.

Figure 4:
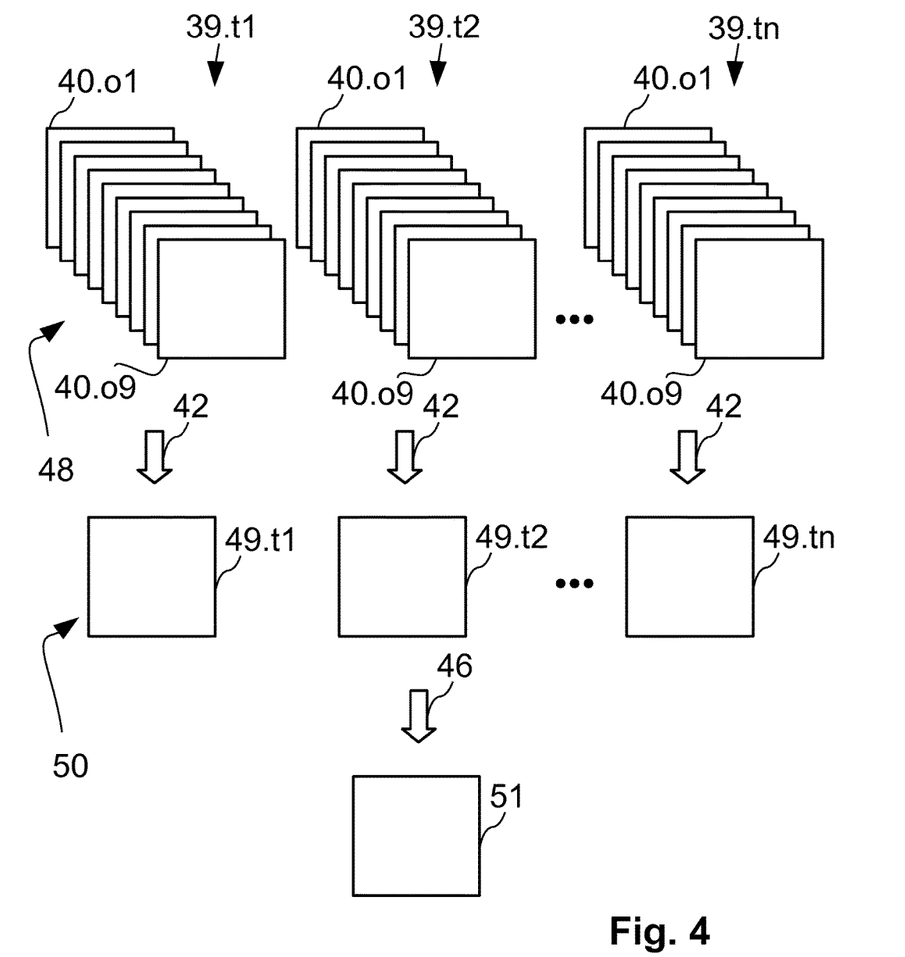
FIG. 4 shows a first embodiment of a method for creating an image with even higher resolution while combining the principles according to FIGS. 2 and 3.

With this proviso, a first method for high-resolution microscopy can now be explained by means of FIG. 4. To this end, sets 39 are repeatedly created, each of which consists of images 40.o1 to 40.o9. This repetition results in a total of n sets 39.t1 to 39.tn. Each set contains the orientations, required for the SIM concept, of the illumination states, which should be clarified by transferring the reference indices from FIG. 2 into FIG. 4. The same thing also applies in the event that the ISM principle is used instead of the SIM principle.

In this case, through the use of Fourier filtration 42, a sequence 50 of raw images, 49.t1 to 49.tn, is created from each set, 49.t1 to 49.tn. These raw images 49 are in chronological intervals and contain image information with a higher resolution than what the microscope provides a priori, due to the use of the SIM principle. The sequence 50 is then converted into a high-resolution image 51 using the cumulant function 46. Its resolution is higher than the resolution in the raw images 49.

Figure 5:
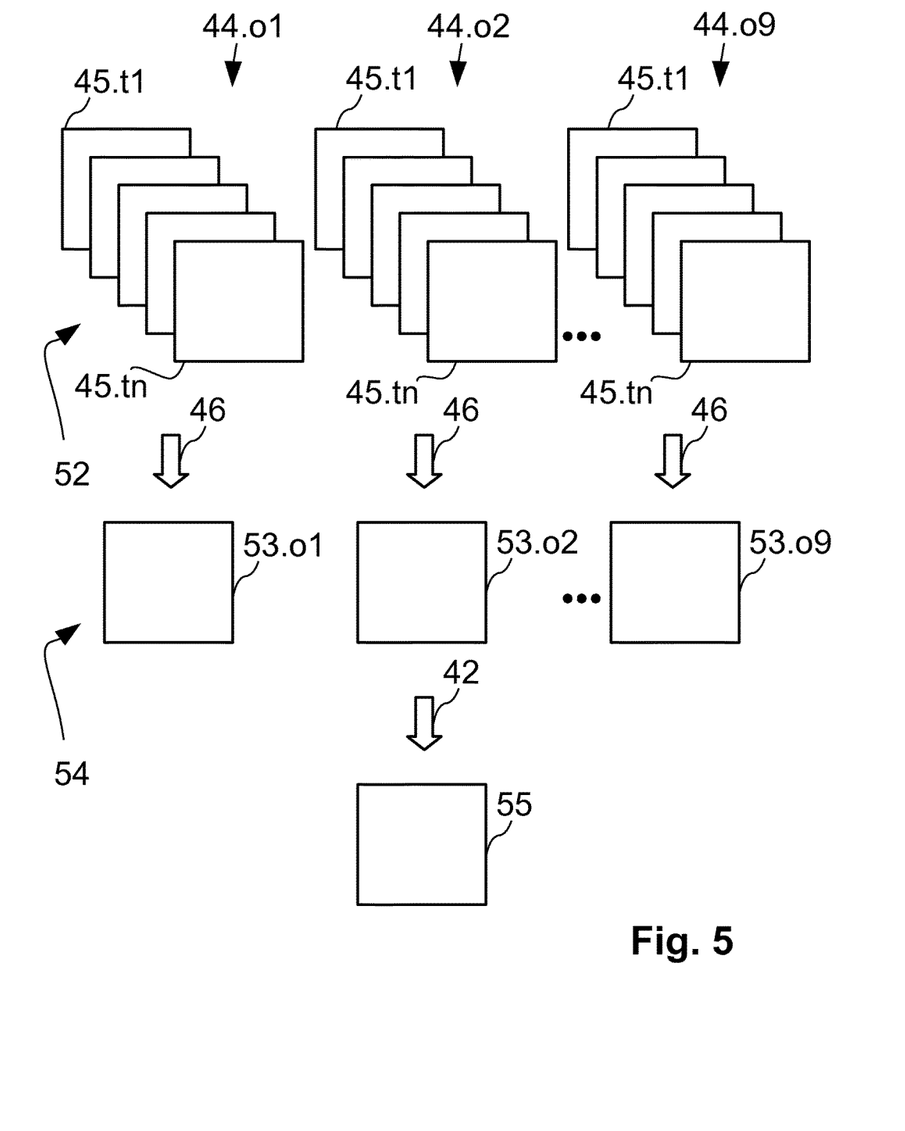
FIG. 5 shows a second embodiment of a method for creating an image with yet even higher resolution also while combining the principles according to FIGS. 2 and 3.

In a second microscopy method, a sequence 54 of images 45 is captured for each orientation, .o1 to .o9, so that there is a separate sequence for each orientation. Each sequence is then converted to a high-resolution raw image using the cumulant function, so that there is a total of one set 54 of raw images, 53.o1 to 53.o9. The set 54 thus contains raw images 53 in the various illumination structures required for the SIM principle. The same thing applies to the use of the ISM principle. Using Fourier filtration 42, the set 54 comprising raw images is then converted into a high-resolution image 55 whose local resolution is higher than that of each raw image 53 whose resolution is respectively even higher than the optics of the microscope 1 would actually allow due to the physical limits.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically disclosed.

What is claimed is:

1. A microscopy method to create a high-resolution image (55) of a sample (2), the microscopy method comprising the steps of:
   a) using one of a sample that does not emit statistically flashing luminescent radiation after excitation and providing the sample with a marker that emits statistically flashing luminescent radiation after excitation, and a sample that emits locally distributed, statistically flashing luminescent radiation after excitation;
   b) exciting the sample to a luminescent state through repeated illumination of the sample in various illumination states of structured illumination, each of the various illumination states being implemented using one of:
      at least three rotational positions of the structured illumination and one of at least three displacement positions in the structured illumination per rotational position; and
      at least three rotational positions of the structured illumination and one of at least three scan positions in the structured illumination per rotational position;
   c) repeatedly imaging the luminescent sample onto a detector in each of the various illumination states, to obtain a sequence of images for each of the various illumination states;
   d) for each of the various illumination states, creating a raw image that has local resolution increased beyond the optical resolution of the image from each sequence of images by employing a cumulant function that evaluates intensity fluctuations in the sequence of images caused by the flashing; and
   e) using Fourier filtration to convert the raw images created in step d) into a high-resolution image, which has a local resolution higher than that of the raw image created from each sequence of images and a lateral resolution beyond the optical diffraction limit.

2. A microscopy method to create a high-resolution image of a sample, the microscopy method comprising the steps of:
   a) providing the sample with a marker that emits statistically flashing luminescent radiation after excitation, or selecting the sample as one that emits locally distributed, statistically flashing luminescent radiation after excitation;
   b) generating structured illumination using one of a grating, a variably adjustable strip modulator, a DMD, and different scan positions that occur during scanning;
   c) exciting the sample to a state of luminescence through the structured illumination, wherein the sample is repeatedly illuminated with a set of various illumination states of the structured illumination, each of the various illumination states being implemented using one of:
      at least three rotational positions of the structured illumination and one of at least three displacement positions in the structured illumination per rotational position; and
      at least three rotational positions of the structured illumination and one of at least three scan positions in the structured illumination per rotational position;
   d) imaging the luminescent sample for each set of various illumination states and imaging each of the various illumination states of the set of various illumination states onto a detector to obtain a sequence of sets, each of which comprises one image for each different illumination state;
   e) using Fourier filtration to convert the sequence of sets created in step d) into a sequence of raw images with local resolution higher than the optical resolution of a single image from each set, to obtain the sequence of raw images;
   f) creating the high-resolution image, which has a local resolution higher than that of the raw images and a lateral resolution beyond the optical diffraction limit, from the sequence of raw images by means of a cumulant function, which evaluates the intensity fluctuations in the sequence caused by the flashing.

3. The method according to claim 2, wherein in step a), the sample is provided with a marker that emits flashing luminescent radiation at an average flashing rate, and, in step c), the acquisition period of each image is selected such that the time it takes to create a set of various illumination states is no greater than the inverse of the average flashing rate.

4. The method according to claim 3, wherein the average flashing rate is no greater than 1/10 of the inverse of the average flashing rate.

5. The method according to claim 2, wherein in step a), the sample is used that emits flashing luminescent radiation at an average flashing rate, and, in step c), the acquisition period of each image is selected such that the time it takes to create a set of various illumination states is no greater than the inverse of the average flashing rate.

6. The method according to claim 5, wherein the average flashing rate is no greater than 1/10 of the inverse of the average flashing rate.

7. The method according to claim 1, wherein the sample is imaged onto a surface detector having a number of pixels.

8. A microscope for creating a high-resolution image of a sample, in which the sample is provided with a marker that emits statistically flashing luminescent radiation after excitation, or a sample that emits locally distributed, statistically flashing luminescent radiation after excitation, wherein the microscope comprises:
 a detector;
 a detection beam path;
 a detection beam path that images the sample onto the detector;
 one of a grating, a variably adjustable strip modulator, and a DMD in the illumination beam path for generating structured illumination having various illumination states,
 an illumination beam path that illuminates the sample to a state of excitation of luminescence through the structured illumination;
 a control device that controls the microscope such that the sample is repeatedly illuminated in the various illumination states of structured illumination, and the luminescent sample is repeatedly imaged onto the detector in each of the various illumination states so that a sequence of images is obtained for each of the various illumination states; and
 an image field rotator having a plurality of rotational positions, wherein each of the various illumination states is implemented using one of:
  at least three rotational positions of the structured illumination and one of at least three displacement positions in the structured illumination per rotational position; and
  at least three rotational positions of the structured illumination and one of at least three scan positions in the structured illumination per rotational position,
 wherein:
 the control device creates a raw image, having a local resolution beyond the optical resolution of the image imaged on the detector, from each image sequence by means of a cumulant function that evaluates intensity fluctuations in the sequence of images caused by the flashing, so that a high-resolution raw image is obtained for each of the various illumination states; and
 the control device creates a high-resolution image, which has a local resolution higher than that of the individual images, from the raw images obtained through Fourier filtration processing.

9. A microscope for creating a high-resolution image of a sample, in which the sample is provided with a marker that emits statistically flashing luminescent radiation after excitation, or a sample is used that emits locally distributed, statistically flashing luminescent radiation after excitation, wherein he microscope comprises:
 a detector;
 a detection beam path;
 one of a grating, a variably adjustable strip modulator, and a DMD in the illumination beam path for generating structured illumination having various illumination states,
 an illumination beam path that illuminates the sample to a state of excitation of luminescence through the structured illumination;
 a control device that controls the microscope such that the sample is repeatedly illuminated with a set of various illumination states of structured illumination, and the luminescent sample in each set and there in each of the illumination states is repeatedly imaged onto a detector, so that a sequence of sets, each of which comprises one image for each of the different illumination states, is obtained; and
 an image field rotator having a plurality of rotational positions, wherein each of the various illumination states being implemented using one of:
  at least three rotational positions of the structured illumination and one of at least three displacement positions in the structured illumination per rotational position; and
  at least three rotational positions of the structured illumination and one of at least three scan positions in the structured illumination per rotational position,
 wherein:
 the control device creates a raw image with local resolution higher than the optical resolution of the image imaged on the detector, so that a sequence of raw images is obtained from each set through Fourier filtration; and
 the control device creates the high-resolution image, which has a local resolution higher than that of the raw images, from the sequence of raw images by means of a cumulant function, which evaluates the intensity fluctuations in the sequence caused by the flashing.

10. The microscope according to claim 9, wherein the sample or its single marker emits flashing luminescent radiation at an average flashing rate, and the acquisition period of each image is specified such that the time it takes to create a set is no greater than the inverse of the average flashing rate, or preferably no greater than 1/10 of the inverse value.

11. The microscope according to claim 8, further comprising an image field rotator, wherein the various illumination states have three rotational positions and at least three displacement positions in the structured illumination per rotational position of the image field rotator, and the detection beam path images the sample onto the detector wherein the detector has a surface having a number of pixels.

12. The microscope according to claim 9, further comprising an image field rotator, wherein the various illumination states have three rotational positions and at least three displacement positions in the structured illumination per rotational position of the image field rotator, and the detection beam path images the sample onto the detector wherein the detector has a surface having a number of pixels.

* * * * *